United States Patent [19]
Nichols

[11] Patent Number: 6,074,636
[45] Date of Patent: Jun. 13, 2000

[54] METHOD OF USING CELL SURFACE RECEPTOR TARGETED MOLECULES FOR THE TREATMENT OF VIRAL DISEASES

[75] Inventor: Jean C. Nichols, Wayland, Mass.

[73] Assignee: Seragen, Inc., Hopkinton, Mass.

[21] Appl. No.: 08/465,541

[22] Filed: Jun. 5, 1995

Related U.S. Application Data

[63] Continuation of application No. 08/289,128, Aug. 11, 1994, abandoned, which is a continuation of application No. 08/053,557, Apr. 27, 1993, abandoned, which is a continuation of application No. 07/914,492, Jul. 15, 1992, abandoned, which is a continuation of application No. 07/665,762, Mar. 7, 1991, abandoned.

[51] Int. Cl.$^7$ .................................................. A61K 38/20
[52] U.S. Cl. .................. 424/85.2; 424/143.1; 424/144.1; 514/2; 514/8; 514/12; 514/885
[58] Field of Search ................................. 424/85.1, 85.2, 424/143.1, 144.1; 514/2, 8, 12, 885, 21

[56] References Cited

FOREIGN PATENT DOCUMENTS

| 0396387 | 11/1990 | European Pat. Off. . |
| 9101004 | 1/1991 | WIPO . |

OTHER PUBLICATIONS

Ogata et al. Proc. Natl. Acad. Sci. USA 86:4215–4219 (1989).
Siegall et al. Proc. Natl Acad. Sci. USA 85:9738–9741 (1988).
Waters et al. Eur. J. Immun. 20:785–791 (1990).
Traunecker et al., "Highly Efficient Neutralization of HIV with Recombinant CD4–Immunoglobulin Molecules" *Nature* 339:68, 1989.
Chaudhary et al., "Selective Killing of HIV–Infected Cells by Recombinant Human CD4–Pseudomonas", *Nature* 335–369, 1988.
Till et al., "HIV–Infected Cells are Killed by rCD4–Ricin A Chain", *Science* 242:1166, 1988.
Capon et al., "Designing CD4 Immunoadhesins for AIDS Therapy", *Nature* 337:525, 1989.
Kronke et al., *Blood,* vol. 65(6), 1985, pp. 1416–1421.
Kronke et al., *Cancer Res,* vol. 46, 1986, pp. 3295–3298.
Kiyokawa et al., *Cancer Res,* vol. 49, 1989, pp. 4042–4046.
Schwartz et al., "Interleukin–2 in the Treatment of HIV Disease", *Biotherapy,* vol. 2, pp. 119–136, 1990.
Walz et al., PNAS, vol. 86, p. 9485, 1989.
Kamio et al., *Blood,* vol. 75, p. 415, 1990.
Aullo et a., Embo J., vol. 11, p. 575, 1992.
Williams et al., JBC, vol. 265, p. 1185, 1990.
Fahey et al., Clin. Exp. Immunology, vol. 22, p. 10, 1992.
Fahey et al. (1992) Clin. exp. Immunol. vol. 88, pp. 1–5.
Schwartz et al. (1990) Biotherapy vol. 2, pp. 119–136.
Aullo et al. (1992) The Embo Journal. vol. 11, No. 2 pp. 575–583.
Kamio et al. (1990) Blood vol. 75, No. 2, pp. 415–420.
Walz et al. (1989) Proc. Nalt. Acad. Sci. U.S.A, vol. 86, pp. 9485–9488.
Williams et al. (1990) The Journal of Biological Chemistry vol. 265 No. 20 pp. 11885–11889.
Nichols, et al., Bacterial Protein Toxins, Zbl. Bakt, Suppl. 19:479–487 (1990).

*Primary Examiner*—Prema Mertz
*Attorney, Agent, or Firm*—Lerner, David, Littenberg, Krumholz & Mentlik, LLP

[57] ABSTRACT

The invention features a method for treating a patient infected with a virus. The method includes administering to the patient a molecule which is capable of specifically binding to a proteinaceous cell receptor expressed on a cell of the patient which cell contributes to the disease state of the patient, the molecule being capable of decreasing the viability of the cell.

20 Claims, 1 Drawing Sheet

METHOD OF USING CELL SURFACE RECEPTOR TARGETED MOLECULES FOR THE TREATMENT OF VIRAL DISEASES

This is continuation of application Ser. No. 08/289,128 filed on Aug. 11, 1994, now abandoned, which is a continuation of Ser. No. 08/053,557, filed Apr. 27, 1993, now abandoned, which was a continuation of Ser. No. 07/914,492, filed Jul. 15, 1992, now abandoned, which was a continuation of Ser. No. 07/665,762, filed Mar. 7, 1991, now abandoned.

BACKGROUND OF THE INVENTION

This invention relates to the treatment of diseases associated with viral infection.

Human immunodeficiency virus (HIV), the etiologic agent of acquired immunodeficiency syndrome (AIDS), is a retrovirus which selectively infects certain immune system cells, including T4 (CD4+) lymphocytes and CD4+ cells of the monocyte/macrophage lineage. In its advanced stages, HIV infection causes immune system failure and renders the victim susceptible to opportunistic infections and neoplasms. In the absence of effective treatment, the mortality rate for AIDS patients approaches 100% (Fauci, *Science* 239:617, 1988).

T4 lymphocytes play a central role in many immune system functions, and the cytopathic effect of HIV on infected T4 lymphocytes is thought to be responsible for the devastating effect of HIV infection. Active viral replication usually leads to the death of the host cell. However, in certain host cells the virus does not immediately replicate, and these cells become chronically or latently infected (Fauci, supra). Chronically infected cells express viral proteins at a low level; latently infected cells have an integrated provirus but do not express viral proteins. Although viral replication does not occur in chronically or latently infected cells until the cells are activated, these cells can serve as a reservoir of HIV in the body.

Previous approaches to slowing the progression of HIV infection include the use of antibodies and antibody-like molecules directed against HIV coat proteins, drugs that inhibit viral replication, an cytotoxins targeted to infected cells that express HIV encoded proteins.

Cytotoxic hybrid proteins composed of a cytotoxin fused to part of the CD4 receptor have been proposed as a way to destroy cells expressing HIV encoded proteins. This approach relies on the fact that the HIV envelope protein, gp120, recognizes the CD4 receptor, which is present on T4 lymphocytes and certain cells of the monocyte/macrophage lineage. Thus, a soluble derivative of CD4 might be used to target a cytotoxin to HIV infected cells that express surface gp120. This approach is likely to be most effective against productively infected cells in which HIV is replicating; under these circumstances there is likely to be significant expression of gp120 on the cell's surface. Chaudhary et al. (*Nature* 335:369, 1988) found that administration of a CD4-Pseudomonas exotoxin hybrid protein to a lymphocytic cell line chronically infected with HIV causes a decrease in overall protein synthesis. Till et al. (*Science* 242:1166, 1988) found that a CD4-ricin A fusion protein decreases DNA synthesis in cultures of chronically infected H9 cells. In a variation of this strategy, Capon et al. (*Nature* 337:529, 1989) designed a hybrid protein composed of soluble CD4 and the constant region of an antibody. This molecule is designed to direct immune system response to HIV and the HIV coat protein, gp120. Another molecule of this general type has been shown to activate complement (Traunecker et al., *Nature* 339:78, 1989).

Human T-lymphotropic retrovius type I (HTLV-I) is associated with adult T-cell leukemia and may play a role in other diseases including tropical spastic paraparesis and HTLV-I associated myelopathy.

Epstein-Barr virus (EBV) is a B lymphotropic human herpes virus. The majority of people infected with EBV develop infectious mononucleosis. EBV is also associated with African Burkitt's lymphoma, anaplastic nasopharyngeal carcinoma, and, in immunocompromised individuals, lymphocytic (usually B-cell) lymphomas.

SUMMARY OF THE INVENTION

In general the invention features a method for treating a patient infected with a virus; the method includes administering to the patient a molecule which is capable of specifically binding to a proteinaceous cell receptor expressed on a cell of the patient and which contributes to the disease state of the patient, the molecule being capable of decreasing the viability of the cell. By "cell receptor" is meant molecule which is encoded by cellular DNA, binds a ligand, and is expressed so that at least a portion of the molecule is exposed on the cell surface. By "specifically binding" is meant that the molecule does not substantially bind to other cell receptors or cell surface proteins. By "reduces viability" is meant kills or interferes with proliferation. By "ligand" is meant a molecule which is capable of binding to a protein.

In preferred embodiments, the virus is human immunodeficiency virus; the virus is HTLV-I; the virus is EBV; the proteinaceous cell receptor is the high affinity interleukin-2 receptor; the molecule kills cells bearing the cell receptor; the molecule is a hybrid molecule which includes a first and a second portion joined together covalently, the first portion includes a molecule capable of decreasing cell viability and the second portion includes a molecule capable of specifically binding to the cell receptor. In more preferred embodiments, the second portion of the hybrid molecule includes all or a binding portion of an antibody specific for the cell receptor; the second portion of the hybrid molecule includes all or a binding portion of a ligand for the cell receptor. By a "binding portion" is meant a portion capable of specifically binding to a cell receptor. In still more preferred embodiments, the ligand is a growth factor; the ligand is an interleukin. In yet more preferred embodiments, the interleukin is interleukin-4; the interleukin is interleukin-6.

In a preferred embodiment, the first portion of the hybrid molecule includes a cytotoxin. In a more preferred embodiment, the cytotoxin is a fragment of a peptide toxin which is enzymatically active but which does not possess generalized eukaryotic receptor biding activity. In an even more preferred embodiment, the fragment of a peptide toxin includes fragment A of diphtheria toxin and enough of fragment B of diphtheria toxin to form a pore in a cell membrane. In still more preferred embodiments, the molecule is $DAB_{486}IL-2$; the molecule is $DAB_{389}IL-4$; the molecule is $DAB_{389}IL-6$.

In a preferred embodiment, the molecule includes all or a binding portion of an antibody specific for the cell receptor. In a more preferred embodiment, the antibody is a complement activating antibody.

The invention provides a method for treating viral diseases. The method eliminates or neutralizes cells which bear a cell surface receptor which is induced following viral infection of the patient; this is accomplished by targeting a molecule (e.g., a cytotoxin or lytic antibody) to that receptor. The cells targeted can be either infected or uninfected cells of the patient who is infected with the virus. Viruses can cause infected cells to express a cell surface receptor; in some cases, the viral disease causes some uninfected cells to express certain receptors, and this expression may contribute to the pathophysiology of the viral disease. Virally induced expression of a receptor a particular cell includes: expression by a cell (whether infected or uninfected) of a receptor which would normally never be expressed by that cell (or cell type); expression by a cell (whether infected or uninfected) of a receptor which can normally be expressed by that cell (or cell type) but which is normally expressed only under certain circumstances; and virally associated expression of a receptor by a cell which expression is significantly higher than the expression by an unaffected cell. For example, HTLV-I infected T-lymphocytes persistently express the high-affinity interleukin-2 receptor; normally this receptor is expressed by T-lymphocytes only after cell activation. In other instances, including HIV infection itself, productive viral replication does not occur until a circumstantial event triggers or markedly elevates expression of a receptor in association with a state of cellular activation. The method of the invention is applicable to this situation as well. To summarize, virally associated expression of a cell receptor includes: any expression of a cell receptor that is induced, directly or indirectly, by the virus; cell receptor expression which follows infection with the virus; and cell receptor expression which contribute to the disease state.

The method of the invention can be used to treat HIV infection by killing or neutralizing HIV-infected and harmful uninfected cells that express the high affinity interleukin-2 receptor (IL-2R). In vitro experiments (see below) have demonstrated that the high affinity IL-2 receptor is expressed on the surface of HIV-infected cells prior to expression of HIV encoded proteins, and the method of the invention is thus useful for destroying HIV infected lymphocytes and monocytes/macrophage both before and after viral replication has occurred. Accordingly, the method of the invention is capable of elimanating HIV-infected cells at an early stage, prior to the production and release of mature virus. The method of the invention can eliminate chronically and latently infected cells that express the high affinity IL-2R. Because the method of the invention targets a protein encoded by cellular DNA rather than an HIV-encoded protein, the method is useful for treating patients infected with any strain of HIV. HIV is known to undergo rapid mutation particularly in the sequences encoding the coat protein and the reverse transcriptase. The method of the invention will be effective against HIV regardless of the exact structure of the coat protein or the reverse transcriptase and thus should be effective against all HIV variants. This is important because the HIV in a given patient is likely to consist of a cohort of viral species. The method of the invention will be effective against all forms of HIV (e.g., HIV-1 and HIV-2) providing that following infection, expression of a cell surface receptor, such as IL-2R, is induced.

Infection by EBV or HTLV-I is also thought to cause expression of the interleukin-2 receptor on the surfaces of cells which would otherwise not express that receptor. Thus, the method of the invention may be used for treatment of diseases caused by infection with EBV or HTLV-I.

Generally, the method of the invention will be useful for treatment of any viral infection which is associated with the induction of expression of a cell surface receptor. In addition to eliminating or neutralizing virally infected cells, the method of the will be useful for treatment of virally caused diseases in which virally induced expression of a cell surface receptor contributes to the course of the infection or to the pathophysiology of the disease. Although the interleukin-2 receptor is suggested as a target in the examples below, the method of the invention can be use to target cells bearing other virally induced receptors (e.g., the interleukin-4 receptor or the interleukin-6 receptor).

HIV and Immune Cell Activation

Immune cell activation and accompanying cytokine production play an extremely important role in the progression of HIV infection and in the pathologic effects of HIV infection.

Activation of HIV infected cells has been shown to be important for the establishment of a productive infection. The activation signals which have been shown to be capable of inducing cell activation and virus production include: phorbol esters, UV irradiation, antigens, mitogens (e.g., phytohemagglutinin), and cytokines such as tumor necrosis factor $\alpha$, tumor necrosis factor $\beta$, granulocytemacrophage colony-stimulating factor, and interleukin-6 (see McCune, Cell 64:351, 1991 for a review). Resting T cells, which represent the vast majority of T-cells in vivo, can bind and take up HIV; these cells begin to synthesize viral DNA, but they fail to convert HIV genomic RNA to full length double-stranded DNA (Zack et al., Cell 61:213, 1990). Thus, infection of resting cells may lead to an eclipsed or latent viral state which can be converted to a productive viral infection only after cell activation. In other cases, the infected cell may be briefly activated, allowing viral integration and render the cell fully permissive for HIV infection. This cell can then cycle back to a resting state, possibly allowing the establishment of a second latent infection. In vitro studies have demonstrated that infected cells may remain in a latent state in which the viral genome is integrated, but viral transcription occurs at a very low level (Pomecantz et al., Cell 61:1271, 1990). Viral RNA production in such latently infected cells is dramatically increased by cell activation. Cell activation triggers high level expression of virally encoded proteins and viral replication. High level expression and viral replication leads to a burst of virion release and host cell death. The fact that mitogen- and antigen-induced cell activation induces HIV expression in T-lymphocytes and monocytes/macrophages has led to the hypothesis that cytokines play an important role in the activation of HIV. A protein, NF-κB, whose expression is induced during normal immune cell activation, may be responsible for the enhanced HIV expression which accompanies cell activation. This protein binds to sequences present in the HIV enhancer and, along with other transcription factors, contributes to the activation of HIV expression (Lenardo et al., Cell 58:227, 1989; Böhnlein et al., Cell 53:827, 1988) and to the activation of IL-2R expression (see below). It appears that normal immune cell activation and accompanying cytokine production may contribute to the progression of HIV infection at several points including: establishment of HIV infection, enhancement of viral protein expression and replication in productively infected cells, and escape from latency. Accordingly, administration of immunostimulants to patients suffering from HIV-induced immunosuppression may, paradoxically, be detrimental since such agents may induce activation and proliferation of resting T-lymphocytes and monocytes/macrophages and thus enhance viral spread.

HIV may itself initiate immune cell activation and interleukin-2 receptor expression. In vitro experiments have demonstrated that exposure of CD4+ lymphocytes or CD4+ cells of the monocyte/macrophage lineage to HIV or purified gp120 results in cell activation an expression of the p55 subunit of the high-affinity interleukin-2 receptor, a molecule which is not normally expressed on the surface of resting cells (Kornfeld et al., *Nature* 35:445, 1988; Allen et al. *J. Clin. Invest.* 85:192, 1990). These results are consistent with the observed increase in surface IL-2 receptor on the monocytes of HIV infected patients (Allen et al., supra) and with the observed increase in soluble IL-2R in the serum of HIV infected individuals (Prince et al., *J. Immmunol.* 140:1139, 1988; Sethi et al., *Immunol. Lett.* 13:179, 1986). This HIV-triggered expression of surface p55 occurs prior to expression of HIV encoded proteins (Kornfeld et al., supra; Allen et al. supra; Fields et al., *Nature* 333:278, 1988; Wahl et al., *Proc. Natl. Acad. Sci. USA* 86:621, 1989). Since purified gp120 can activate uninfected cells, soluble gp120 may activate latently infected cells and initiate a productive infection. In addition, soluble gp120 may activate uninfected cells thereby producing both a favorable environment for subsequent infection of those cells and more of the cytokines and inflammatory mediators which contribute to the generalized immunological dysfunction observed during the course of AIDS. It is not known to what extent exposure to HIV or soluble gp120 activates lymphocytes and monocytes/macrophages in vivo.

The method of the invention can eliminate or neutralize any cell which inappropriately expresses the high affinity IL-2R as a result of HIV iffection or contact with HIV or soluble gp120. Resting lymphocytes and monocytes/macrophages do not express the high affinity IL-2R, and thus are unaffected.

Cytokines may also play a more indirect role in the pathology of HIV infection. As described above, exposure of lymphocytes and monocytes/macrophages soluble gp120 may induce immune cell activation (Kornfeld et al., supra; Allen et al., supra). While these cells are not infected, their activation may adversely affect immune system function. Activated cells undergo premature differentiation and thus become refractory to activation by second immunologic stimulus. This phenomenon has been proposed as an explanation for the fact that the many of the immune cells of HIV infected individuals are phenotypically differentiated but functionally impaired (Allen et al., supra). Further, the cytokines and inflammatory mediators produced by activated cells may have adverse metabolic and immunological effects.

The importance of cytokines in the progression of HIV infection and in the pathologic effects of HIV infection suggests that it may be possible to treat HIV infection by interfering with cytokine action, for example, by blocking cytokine receptors. Such an approach can interfere with both HIV infection and the pathological effects of excess cytokine expression. This approach can be used on its own or to supplement receptor-targeted cytotoxin mediated elimination or neutralization of cells bearing a virally induced receptor.

Described in detail below is an approach to treating HIV infection by targeting molecules to cells bearing the interleukin-2 receptor. However, the method of the invention is not limited to the targeting of cells bearing this receptor. In treatment of HIV infection it may be important to target cells bearing other receptors (e.g., the interleukin-6 receptor or the interleukin-4 receptor). For example, if B-cell hyperactivation contributes to the progression of HIV (Amadori et al., *Immunol Today* 11:374, 1990), drugs which target cytokine receptors present on activated B-cells may indirectly assist in controlling HIV infection. In addition, to the extent that hyperactivation of immune cells contributes to the disruption of normal immune function observed in HIV infection, molecules targeted to activated cells via a cytokine receptor may provide a valuable therapeutic approach even when the cell targeted is not itself infected. For example, the method of the invention may be useful for treatment of AIDS-related psoriasis. Psoriasis is characterized by the hyperproliferation of epidermal cells, and IL-2R is known to be present in the dermis of psoriatic plaques (Gottlieb et al., *J. Am. Acad. Derm.* 18:6, 1988). Since the epidermis is a part of the immune system and expresses a full complement of cytokines, many of which (e.g., IL-2, TNF and GM-CSF) are thought to play a role in psoriasis (Duvic, *J. Invest. Derm.* 95:38S, 1990), the receptors for these cytokines may provide useful targets according to the method of the invention. The method of the invention will also be useful for treating some neoplasms that arise in the later stages of HIV infection and which involve IL-2R bearing cells (e.g., Kaposi's sarcoma, and AIDS associated lymphomas).

HTLV, EBV and Immune Cell Activation

HTLV-I infection of T-lymphocytes is generally associated with persistent expression of the high affinity interleukin-2 receptor. This is in contrast to the transient expression of the high affinity interleukin-2 observed after normal cell activation. Persistent expression of the high affinity interleukin-2 receptor is thought to be mediated by the HTLV- tat-I gene product which induces expression of NF-κB, powerful transcriptional activator. NF-κB in turn stimulates the expression of the p55 subunit of the interleukin-2 receptor. This subunit in combination with the p70 subunit, which is constitutively expressed, forms the high affinity interleukin-2 receptor. HTLV-I infected patients have a high degree of spontaneous lymphocyte proliferation, consistent with an antigen-independent increase in interleukin-2 receptor expression. Further, persistent expression of the high affinity receptor IL-2R may contribute to HTLV-I mediated cell transformation. Infection by HTLV-II, a related retrovirus also causes an increase in antigen-independent lymphocyte proliferation and may also be associated with an increase in interleukin-2 receptor expression. Thus, IL-2R targeted molecules will be useful for treatment of HTLV-I or HTLV-II infection.

As outlined above, NF-κB plays a role in the pathology of both HIV and HTLV-I expression; For example, the HIV enhancer has two binding sites for NF-κB, and induction of NF-κB induces viral transcription. Since NF-κB is activated by many of the same signals which activate T-cells, including mitogens, phorbol esters, antibodies against cell surface markers which mimic physiologic T cell activation, and activators of protein kinase C, NF-κB may play an important role in the course of HIV infection. Other viruses, including cytomegalovirus have NF-κB binding sites within their enhancers. Further, cytomegalovirus and hepatitis virus B, like HTLV-I, encode trans-activators which induce NF-κB expression. A number of viruses induce NF-κB expression, and any such virus may also induce expression of interleukin-2 receptor on the surface of cells which they infect. To the extent which expression of the receptor (or some other receptor) is induced, diseases caused by such viruses may be treated by the method of the invention.

EBV infection is known to induce expression of the high-affinity interleukin-2 receptor on infected cells. Accordingly the method of the invention can be used to kill or neutralize EBV infected cells.

Other features and advantages of the invention will be apparent from the following description of the preferred embodiments thereof, and from the claims.

DETAILED DESCRIPTION

The drawings will first briefly be described.

Drawings

MOLECULES USEFUL IN THE METHOD OF THE INVENTION

Figure 1:
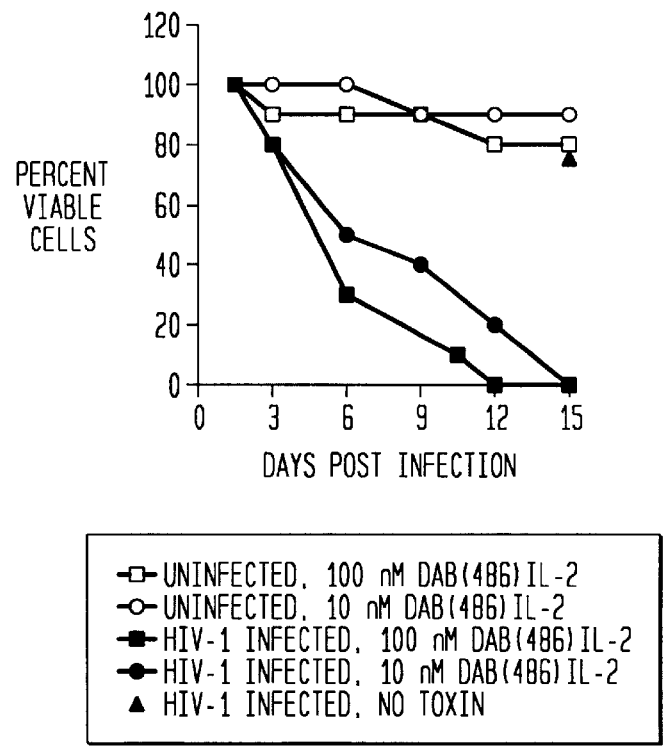
FIG. 1 is a graphical representation of the effect of $DAB_{486}IL$-2 on viability of both HIV-infected and uninfected CD4+ T cells. The percentage of viable cells is presented as a function of the number of days post infection.

In general, there are three ways in which the molecules useful in the invention can act: (1) the molecule can kill a cell because the molecule has a cytotoxic domain; (2) the molecule (an antibody) can cause cell lysis by inducing complement; and (3) the molecule can block binding or uptake of receptor's ligand. In all three cases the molecule must be targeted to receptor bearing cells; this is accomplished by including the receptor's ligand (or a portion or derivative thereof) or an anti-receptor antibody as part of the molecule.

Interleukin-2 receptor targeted molecules useful for treatment of HIV infection provide examples of each of these three approaches. A fusion molecule which includes the IL-2 receptor binding portion of IL-2 and a cytotoxin can be used to kill HIV infected activated lymphocytes and monocytes/macrophages. This molecule can also kill uninfected IL-2 receptor-bearing cells. Such uninfected cells may contribute to the disease state. Similarly, the second type of molecule described above, a complement fixing antibody, in this instance directed against the IL-2 receptor, can eliminate infected and uninfected, IL-2 receptor-bearing cells in a patient infected with HIV. In this example, the third type of molecule could be a molecule that blocks binding of IL-2 to its receptor. This molecule would prevent infected cells from receiving a proliferation signal from IL-2 and thus could slow the spread of HIV infection.

Molecules useful for killing or neutralizing IL-2R bearing cells of HIV infected individuals can take a number of forms. When IL-2 itself is the targeting agent, the molecule can be a cytotoxic hybrid molecule in which IL-2 is fused to a toxin molecule, preferably a polypeptide toxin. Derivatives of IL-2 which bind to IL-2R, lack IL-2 activity and block binding and/or uptake of bona fide IL-2 are useful in the method of the invention because they will prevent IL-2-induced proliferation of IL-2R bearing cells. When an anti-IL-2R antibody is the targeting agent, a cytotoxic hybrid molecule can be formed by fusing all or part of the antibody to a cytotoxin. The effectiveness of such an antibody/toxin hybrid, like that of an IL-2/toxin hybrid, depends on the hybrid molecule being taken up by cells to which it binds. Anti-IL-2R antibodies which block binding and/or uptake of IL-2 are also useful in the method of the invention. Lytic anti-IL-2R antibodies are useful in the invention because they can direct complement against IL-2R-bearing cells and thus cause their lysis.

Some the molecules can be hybrid molecules formed by the fusion of all or part of two or more molecules. The hybrid molecule can be a hybrid protein encoded by a recombinant DNA molecule, in which case the two domains are joined (directly or through an intermediary domain) by a peptide bond. Alternatively, two domains can be produced separately and joined by a covalent bond in a separate chemical linkage step. In some cases, the cytotoxic domain of a hybrid molecule may itself be derived from two separate molecules.

Interleukin-2 as a Targeting Agent

IL-2 or any IL-2 receptor binding derivative thereof can be used as a targeting agent for a cytotoxin. The DNA and amino acid sequences of IL-2 are known (Tadatsugu et al., *Nature* 302:305, 1983), and its structure has been predicted by x-ray crystallography (Brandhuber et al., *Science* 238:1707, 1987). Analysis of genetically engineered variants of IL-2 has provided some information concerning which residues are important for IL-2R binding (Collins et al., *Proc. Natl. Acad. Sci. USA* 85:7709, 1988) and bioactivity (Cohen et al. *Science* 234:349, 1989; Collins et al., supra). Variants of IL-2 which are useful in the invention include deletion mutants (Genbauffe et al., U.S. Ser. No. 388,557, hereby incorporated by reference) which lack one or more amino acid residues in the region between residue 74 and residue 79 (numbering according to Williams et al., *Nucl. Acids Res*. 16:1045, 1988). These mutants effectively target toxins to IL-2R-bearing cells (Genbauffe et al., supra). Generally, IL-2 variants useful for targeting a cytotoxin must efficiently bind IL-2R and be endocytosed. The ability of various derivatives to bind to the IL-2 receptor can be tested with an IL-2 binding assay described below.

In designing molecules targeted to cells bearing the IL-2 receptor it must be recognized that the IL-2 receptor, like other receptors, has several forms; and it may be desirable to target cells bearing one form and not another. The human interleukin-2 receptor has a high-, an intermediate-, and a low-affinity form. The high affinity receptor has an apparent $K_d$ of ~$10^{-10}$M and is composed of two subunits, p55 and p75 (also called p70). When expressed on the cell surface, both the p75 and p55 subunits are capable of binding IL-2. The p75 subunit corresponds to the intermediate affinity receptor ($K_d$~$8.2\times10^{-10}$M), and p55 subunit corresponds to the low affinity receptor ($K_d$~$1–3\times10^{-8}$M. The p75 subunit is expressed on the surface of resting T cells, natural killer cell monocytes/macrophages, and lymphokine-activated killer (LAK) cell precursors, while the high affinity receptor is expressed on activated T- and B-cells.

In the method of the invention it may be desirable to target only cells bearing the high affinity receptor. In these circumstances useful molecules will eliminate or neutralize cells bearing the high affinity IL-2 receptor at a concentration which leaves cells bearing the intermediate or low affinity receptor largely unaffected. When the molecule, like IL-2 itself, has affinity for all three classes of IL-2 receptor, selectivity can be accomplished by administering the molecule at a concentration which does not permit significant binding to cells bearing lower affinity receptors. A hybrid molecule may have altered receptor affinities compared to IL-2. Such hybrid molecules may be more or less selective for cells bearing the high affinity IL-2 receptor. For example, cells bearing the high-affinity receptor are 500–1000 times more sensitive to $DAB_{486}$IL-2, a fusion protein consisting of part of diphtheria toxin and part of IL-2, than are cells bearing the intermediate-affinity receptor (Waters et al., *Eur. J. Immunol.* 20:785, 1990).

A cytotoxin can be attached to an IL-2 derivative in a number of ways. Preferably, an IL-2/toxin hybrid is a hybrid protein produced by the expression of a fused gene. Alternatively, the cytotoxin and the IL-2 derivative can be produced separately and later coupled by means of a non-peptide covalent bond. Linkage methods are described below.

Interleukin-4 as a Targeting Agent

Interleukin-4 (IL-4) is a cytokine which acts on a variety of cell types. Its receptor is expressed on a number of cell types, including CD4+ T cells and monocytes. IL-4 can act as a T cell growth factor and it is thought to have an influence on IL-2 induced lymphocyte proliferation.

A cytotoxin directed against IL-4 receptor-bearing cells may enhance the effectiveness of molecules directed against IL-2R-bearing cells. The protein and DNA sequence of IL-4 are known (Lee et al., *J. Biol. Chem.* 263:10817, 1988). IL-4 can be used to create hybrid IL-4/toxin molecules similar to IL-2/toxin hybrid molecules.

Monoclonal Antibodies as Targeting Agents

Monoclonal antibodies directed against IL-2R, IL-4R or any cell receptor of choice can be used to direct toxins to cells bearing that receptor. These antibodies or antibody fragments can be fused to a cytotoxin either by virtue of the toxin and the antibody being encoded by a fused gene which encodes a hybrid protein molecule, or by means of a non-peptide covalent bond which is used to join separately produced ligand and toxin molecules. Several useful toxins are described below.

Antibody/toxin hybrids can tested for their ability to kill receptor bearing cells using a toxicity assay similar to that which is des bed below for IL-2R bearing cells.

Toxins

The toxin molecules useful in the method of the invention are preferably toxins, such as peptide toxins, which are significantly cytotoxic only when present intracellularly. Of course, under these circumstances the molecule must be able to enter a cell bearing the targeted receptor. This ability depends on the nature of the molecule and the nature of the cell receptor. For example, cell receptors which naturally allow uptake of a ligand are likely to provide a means for a molecule which includes a toxin to enter a cell bearing that receptor. Preferably, a peptide toxin is fused to an IL-2R binding domain by producing a recombinant DNA molecule which encodes a hybrid protein molecule. Such an approach ensures consistency of composition.

Many peptide toxins have a generalized eukaryotic receptor binding domain; in these instances the toxin must be modified to prevent intoxication of non-receptor bearing cells. Any such modifications must be made in a manner which preserves the cytotoxic functions of the molecule (see U.S. Department of Health and Human Services, U.S. Ser. No. 401,412). Potentially useful toxins include, but are not limited to: cholera toxin, ricin, O-Shiga-like toxin (SLT-I, SLT-II, SLT II$_v$), LT toxin, C3 toxin, Shiga toxin, pertussis toxin, tetanus toxin, Pseudomonas exotoxin, alorin, saporin, modeccin, and gelanin.

Diphtheria Toxin-based Molecules

Diphtheria toxin can be use to produce molecules useful in the method of the invention. Diphtheria toxin, whose sequence is known, is described in detail in Murphy U.S. Pat. No. 4,675,382, hereby incorporated by reference. The natural diphtheria toxin molecule secreted by *Corynebacterium diphtheriae* consist of several functional domains which can be characterized, starting at the amino terminal end of the molecule, as enzymatically-active Fragment A (amino acids Gly$_1$–Arg$_{193}$) and Fragment B (amino acids Ser$_{194}$–Ser$_{535}$), which includes a translocation domain and a generalized cell binding domain (amino acid residues 475 through 535).

The process by which diphtheria toxin intoxicates sensitive eukaryotic cells involves at least the following steps: (i) the binding domain of diphtheria toxin binds to specific receptors on the surface of a sensitive cell; (ii) while bound to its receptor, the toxin molecule is internalized into an endocytic vesicle; (iii) either prior to internalization, or within the endocytic vesicle, the toxin molecule undergoes a proteolytic cleavage between fragments A and B; (iv) as the pH of the endocytic vesicle decreases to below 6, the toxin crosses the endosomal membrane, facilitating the delivery of Fragment A into the cytosol; (v) the catalytic activity of Fragment A (i.e., the nicotinamide adenine dinucleotid—dependent adenosine diphosphate (ADP) ribosylation of the eukaryotic protein synthesis factor termed "Elongation Factor 2") causes the death of the intoxicated cell. It is apparent that a single molecule of Fragment A introduced into the cytosol is sufficient to block down the cell's protein synthesis machinery and kill the cell. The mechanism of cell killing by Pseudomonas exotoxin A, and possibly by certain other naturally-occurring toxins, is very similar.

DAB$_{486}$IL-2, a fusion protein in which the receptor binding domain of diphtheria toxin has been replaced by a portion of human IL-2 (Williams et al., *J. Biol. Chem.* 35:20673, 1990; see also Williams et al., *Protein Eng.* 1:493, 1987), is an example of a molecule useful in the method of the invention. This molecule selectively kills IL-2R-expressing tumor cells and lymphocytes (Waters et al., *Eur. J. Immunol.* 20:785, 1990; Kiyokawa et al., *Cancer Res.* 49:4042, 1989). Because of its ability to kill activated lymphocytes, DAB$_{486}$IL-2 has been used to control graft rejection (Pankewycz et al., *Transplantation* 47:318, 1989; Kickman et al., *Transplantation* 47:327, 1989) and to treat certain autoimmune disorders (Forte et al., *2nd International Symposium on Immunotoxins*, 1990).

DAB$_{486}$IL-2 is a chimeric molecule consisting of Met followed by amino acid residues 1 through 485 of the mature diphtheria toxin fused to amino acid residues 2 through 133 of IL-2. Thus, DAB$_{486}$IL-2 includes all of diphtheria toxin fragment A, which encodes the enzymaically active portion of the molecule, and a portion of fragment B. The portion of fragment B present in DAB$_{486}$IL-2 does not include the generalized receptor binding domain but does include the translocation domain which facilitates delivery of the enzymatically active portion into the cytosol.

Experimental Methods

Presented below are experiments which demonstrate that DAB$_{486}$IL-2 can kill HIV-1 infected T cells, selectively eliminate HIV-1 infected cells from mixed cultures of infected and uninfected T cells, and reduce HIV-1 replication in cultures of infected monocytes. DAB$_{486}$IL-2 is also shown to inhibit production of viral proteins in cultures of infected T cells and to block production of infectious HIV-1 in cultures of infected T cells.

Other molecules targeted to IL-2R may be screened using the methods described below.

Preparation of DAB$_{486}$IL-2

DAB$_{486}$IL-2 was produced in *E. coli* harboring the DAB$_{486}$IL-2 encoding plasmid, pDW24 (Williams et al., J. Biol. Chem. 265:20673, 1990, except amp$^r$ is replaced by kan$^r$). The protein was purified by immunoaffinity chromatography and high pressure liquid chromatography (Williams et al., supra).

Killing of HIV-1 Infected T Cells by DAB$_{486}$IL-2

DAB$_{486}$IL-2 at $10^{-8}$M or $10^{-9}$M destroyed HIV-1 infected T cells while having almost no effect on uninfected T cells.

CD4+ T cells were prepared from the peripheral blood of HIV-1 negative donors by negative selection to remove B cells, macrophages, natural killer cells, and CD8+ T cells. B cells and macrophages were removed by passage over glass wool. CD8+ and CD16+ cells were removed using anti-CD8 (OKT8, American Type Culture Collection, Rockville, Md.) and anti-CD16 (Leu 11a, Bectin-Dickinson Mountain View, Calif.) monoclonal antibody coated magnetic beads by the method of Haregewoin et al. (*Nature* 340:309, 1989). Cells were cultured at $2 \times 10^6$/ml in RPMI 1640 (GIBCO/BRL, Bethesda, Md.) and 10% bovine calf serum (GIBCO BRL, Bethesda, Md.) supplemented with lymphocult-T (Boehringer-Mannheim Biochemicals, Indianapolis, Ind.; corresponds to $\sim 10^{-9}$M IL-2). Infections were performed by incubation with HTLVIII$_B$ (prepared from filtered supernatants of infected H9 cells, AIDS Research and Reference Reagent Program NIAID, National Institutes of Health, Bethesda, Md.) for 1 hr at a multiplicity of infection of 10 (calibrated by limiting dilution of H9 cells). DAB$_{486}$IL-2 ($10^{-7}$M or $10^{-8}$M) was added on days one and three post-infection. Cell cultures were split twice weekly, and viability was determined by a trypan blue dye exclusion assay (Kruse et al., eds. *Tissue Culture: Methods and Applications*, Academic press, 1989)

Referring to FIG. 1, treatment of uninfected cells with $10^{-8}$M (open circles) or $10^{-7}$M (open squares) DAB$_{486}$IL-2 only transiently impaired proliferation of T cells in response to $10^{-9}$M IL-2. Further, cultures of uninfected T cells treated with DAB$_{486}$IL-2 and untreated uninfected T cells achieve similar cell densities after two weeks of culturing. In contrast, HIV-1 infected cells were eliminated by incubation with $10^{-8}$M (filled cirles) or $10^{-7}$M (filled squares) DAB$_{486}$IL-2. This toxic effect occurs despite the fact that the cells are cultured in the presence of $10^{-9}$M IL-2 which is required for cell viability and which has a 10- to 100-fold higher affinity for IL-2R than does DAB$_{486}$IL-2 (Waters et al., supra). Infected cells which were not treated with DAB$_{486}$IL-2 were >75% viable after two weeks, demonstrating that the reducton in viability of DAB$_{486}$IL-2 exposed cells is a specific effect and is not due to viral replication.

Selective Killing of HIV-1 Infected Cell by DAB$_{486}$IL-2

DAB$_{486}$IL-2 prevented production of the HIV-1 encoded proteins, gp120, p55, and p24, in mixed cultures of HIV-1 infected and uninfected T cells.

CD4+ T cells prepared and infected as described above were incubated overnight in RPMI 1640 medium containing 10% bovine calf serum and washed three times with the same medium prior to addition of uninfected cells from the same donor. Infected T cells ($10^9$) and uninfected T cells ($10^7$) were cultured in the presence of $10^{-9}$M IL-2 (Lymphocult T) with or without $10^{-8}$M DAB$_{486}$IL-2 at $10^6$ cells/ml. Every two days cells were pelleted, washed twice, and resuspended in fresh IL-2 containing media. DAB$_{486}$IL-2 was added to the treated cultures on days 1 and 3 and was washed out 24 hours later. The untreated cultures were washed according to the same schedule but were not exposed to DAB$_{486}$IL-2. Two weeks after infection, the cells were labelled overnight with $^{35}$S in methionine-free media (GIBCO/BRL, Bethesda, Md.). Proteins were immunoprecipitated (Coligan et al, eds., *Current Protocols in Immunology*, John Wiley & Sons, New York, 1991) with either anti-HIV globulin (NIAID) or the framework anti-MHC class I antibody (W6/32). Immunoprecipitated proteins were separated on SDS gels and visualized by autoradiography.

Figure 2:
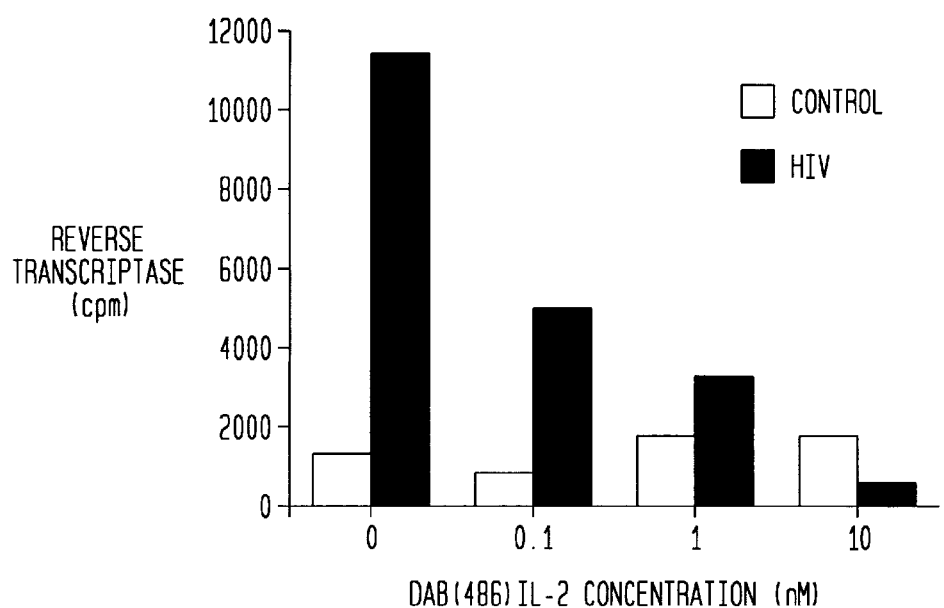
FIG. 2 is a graphical representation of the effect of $DAB_{486}IL$-2 on reverse transcriptase activity present in HIV infected and uninfected monocytes. Reverse transcriptase activity (cpm) is presented as a function of $DAB_{486}IL$-2 concentration (nM) for uninfected (open bars) and HIV-1 (filled bars) infected cells.

Referring to FIG. 2, the proteins in lanes 2–4 were immunoprecipitated using anti-HIV antibody; the proteins in lanes 6–9 were immunoprecipitated using anti-MHC class I antibody; lane 1 has size markers; and the arrows along the right side indicate the expected positions of HIV-1 encoded proteins gp120, p55 and p24. The HIV-1 encoded proteins gp160, p55 and p24 were present in untreated mixed culture (lane 4), but could not be detected in the DAB$_{486}$IL-2 treated culture (lane 5). As expected, normal MHC class I proteins were detected in both the treated (lane 9) and untreated (lane 8) mixed T cell cultures. Unmixed cultures of both uninfected cells (lanes 2 and 6) and infected cells (lanes 3 and 7) served as controls. Cell viability was >95% for both treated and untreated mixed cultures, indicating that the cytotoxic action of DAB$_{486}$IL-2 was limited to infected cells.

DAB$_{486}$IL-2 treatment of mixed cultures of infected and uninfected T cells completely eliminated production of HIV-1 p24 protein. This result was demonstrated by means of a sensitive ELISA assay.

Treated and untreated mixed cultures of infected and uninfected CD4+ T cells were prepared as described above. Cells were pelleted and resuspended twice weekly, and the culture supernatants were assayed for the presence of p24 two days later using an ELISA assay (Abbott, Chicago, Ill.).

Referring to Table 1, in untreated mixed cultures, the level of p24 increased steadily for at least 18 days post-infection. In contrast, p24 was undetectable in mixed cultures which were treated with $10^{-8}$M DAB$_{486}$IL-2. This experiment demonstrates that DAB$_{486}$IL-2 can block all production of an HIV-1 encoded protein.

TABLE 1

Incubation of Mixed T Cell Cultures with DAB$_{486}$IL-2 Eliminates Production of p24 Antigen

| Days Cultured | Infected T-Cells | HIV-1 Infected T-Cells | Mixed T Cell Cultures | Mixed T Cell Cultures + DAB$_{486}$IL-2[2] |
|---|---|---|---|---|
| 6  | 0 | 0    | 0    | 0 |
| 9  | 0 | 256[1] | 0    | 0 |
| 12 | 0 | >500 | 89   | 0 |
| 15 | 0 | >500 | 298  | 0 |
| 18 | 0 | >500 | >500 | 0 |

[1]Picograms of p24 in the supernatant two days after cell washing.
[2]$10^{-8}$M DAB$_{486}$IL-2 add on days 1 and 3.

DAB$_{486}$IL-2 Prevents HIV-1 Infection

Treatment of mixed cultures of infected and uninfected T cell with DAB$_{486}$IL-2 prevented the production of infectious HIV. This was demonsrated by comparing the p24 produced in a co-culture of H9 tumor cells and cells from a DAB$_{486}$IL-2 treated mixed infected and uninfected T cell culture with that produced by culture of H9 tumor cells and cells from an untreated mixed infected and uninfected T cell culture. Despite the fact that H9 cells can be readily infected by HIV, no HIV p24 could be detected in the co-culture supernatant if the mixed infected and uninfected T cells had been treated with DAB$_{486}$IL-2 at least three days prior to their addition to H9 cells.

CD4+ T cells were purified, infected with HIV-1, washed, and then mixed with uninfected cells at a ratio of 1:10 as described above. Cells were cultured in $10^{-9}$M IL-2 with or without $10^{-8}$M DAB$_{486}$IL-2 (added on days 1 and 3). On days 0, 1, 6 and 9, $5 \times 10^5$ T cells were collected, washed and co-cultured with $5 \times 10^5$ uninfected H9 tumor cells (NIAID). Co-cultures were incubate for 6 days prior to measurement of the p24 present in the co-culture supernatant. p24 was measured by the ELISA assay described above.

TABLE 2

Incubation of T Cell Cultures with $DAB_{486}IL-2$ Eliminates Infectious Virus

| Cell Culture | $DAB_{486}IL-2$ | Day of T cell culture post HIV-1 infection | p24[1] day 6 of co-culture |
|---|---|---|---|
| Uninfected T Cells | — | 0 | |
| HIV-1 infected T cells | — | 0 | >500 |
| T Cell mixture | — | 0 | >500 |
| T Cell mixture | $10^{-8}$M | 0 | >500 |
| T Cell mixture | — | 1 | >500 |
| T Cell mixture | $10^{-8}$M | 1 | >500 |
| T Cell mixture | — | 6 | >500 |
| T Cell mixture | $10^{-8}$M | 6 | 0 |
| T Cell mixture | — | 9 | >500 |
| T Cell mixture | $10^{-8}$M | 9 | 0 |

[1]Measured in picograms

Referring to Table 2, when the mixed infected and uninfected T cell culture was not treated with $DAB_{486}IL-2$, p24 was produced in the co-culture supernatant. This result implies that infectious HIV was produced in the untreated mixed cell culture. In contrast, when cells from a $DAB_{486}IL-2$ treated mixed infected an uninfected T cell culture were added to H9 tumor cells 3 or 9 days after the second addition of $DAB_{486}IL-2$, no p24 could be detected in the co-culture supernatant. This result implies that $DAB_{486}IL-2$ treatment was able to clear the mixed infected and uninfected cell culture of infectious HIV. $DAB_{486}IL-2$ treated cultures responded normally to IL-2 and phytohemagglutinin indicating that the treatment is not generally toxic to T cells.

$DAB_{486}IL-2$ Eliminates HIV-1 Replication in Monocytes

Treatment with $DAB_{486}IL-2$ blocked HIV-1 replication in monocytes as judged by a reverse transcriptase assay.

Aliquots of monocytes ($10^7$) purified according to Wahl et al. (*Cell Immunol.* 85:3553, 1984) were suspended in 1 ml of primary macrophage culture supernatant containing HIV-1/HTLV-III$_{Ba-L}$ ($2.5 \times 10^4$ cpm reverse transcriptase activity). As a control, aliquots of monocytes were suspended in RPMI 1640 containing 10% fetal calf serum (FCS, GIBCO/BRL). Infected and control cultures were incubated for 1 h at 37° C. with intermittent gentle agitation. The cells were then washed with RPMI 1640 plus 10% FCS, resuspended in RPMI 1640 containing 10% FCS, antibiotics, and glutamine, plated ($2 \times 10^6$) on chamber slides and incubated at 37° C. $DAB_{486}IL-2$ ($10^{-8}$ to $10^{-10}$M) was added beginning on day 3 (when IL-2R is expected to be present on infected monocytes) and every third day thereafter. Supernatants from the infected and control monocyte cultures were assayed directly for reverse transcriptase activity by a modification of the method of Spira et al. (*J. Clin. Microbiol.* 25:97, 1987). Briefly, 15 µl aliquots of supernatant were removed from each culture, 5 µl of a buffer containing 30% glycerol and 0.5% Triton x-100 was added to each aliquot in order to solubilize ny virus present. 25 µl of a reaction mix containing 5 µCi of $^3$H-thymidine triphosphate (20 Ci/mmol; Du Pont NEN, Boston, Mass.), 0.45 µg poly rA oligo (12–18 bases long; Pharmacia, Piscataway, N.J.), and 10 mM $MgCl_2$ was added to each test aliquot. The reactions were incubated at 37° C. for 2.5 h, and the reaction products were ethanol precipitated.

Referring to FIG. 3, $10^{-8}$M $DAB_{486}IL-2$ virtually eliminated reverse transcriptase activity in HIV-1 infected monocytes (solid bars). Lower $DAB_{486}IL-2$ concentrations inhibited reverse transcriptase activity to a lesser extent. $DAB_{486}IL-2$ did not effect the background measurement of reverse transcriptase activity in uninfected cells (open bars). Further, adherent monocyte/macrophages remaining in the $DAB_{486}IL-2$ treated cultures were viable and morphologically indistinguishable from untreated cells.

Use for $DAB_{486}$ IL-2 for Treatment of Kaposi's Sarcoma

Certain epidermoid cancers and sarcomas can also express functional IL-2 receptors. Accordingly, molecules targeted to cells bearing the IL-2 receptor can be used for treatment of cancers and sarcomas associated with viral diseases. IL-2 receptors were demonstrated on Kaposi's sarcoma cells using B-D phycoerythrin labelled monoclonal anti-TAC (anti-p55) antibody. Two patients with advanced AIDS and disseminated, chemotherapy resistant Kaposi's sarcoma underwent one course of 5 doses of $DAB_{486}IL-2$ administered as a daily 90 min intravenous infusion. Both patients had an approximately 30% regression in their skin lesions.

Preparation of $DAB_{389}IL-4$

A synthetic gene encoding human interleukin-4 was synthesized (Milligen/Biosearch 7500 DNA synthesizer). The IL-4 sequence (Yodota et al., *Proc Nat'l Acad Sci. USA*, 83:58994, 1986) was modified to incorporate *E. coli*-preferred codon usage (deBoer et al., in *Maximizing Gene Expression*, Reznikioff et al., eds., 1986, Butterworths, Boston), and restriction endonuclease cleavage sites were added to facilitate subsequent cloning steps. IL-4 coding sequence (His[1] to Ser[129]) was inserted into pDW27 plasmid. pDW27 is derived from pDW24 (Williams et al., J. Biol. Chem. 265:11885, 1990) by deleting DNA corresponding to amino acids 388 to 485 of native diphtheria toxin.

Cytotoxicity of $DAB_{389}IL-4$

The ability of $DAB_{389}IL-4$ to reduce viability of various cell types was measured using an inhibition of protein synthesis assay; the result of this assay are presented in Table 3. $IC_{50}$ (M) is the concentration of $DAB_{389}IL-4$ required for a 50% decrease in protein synthesis. The rat, Con A-activated, normal spenic lymphocytes were far less sensitive to $DAB_{389}IL-4$ than any of the other cells or cell lines. Since the rat interleukin-4 receptor does not bind human interleukin-4, this result demonstrates the specificity of $DAB_{389}IL-4$. These rat cells are sensitive to a diphtheria toxin/rat interleukin-2 hybrid molecule.

TABLE 3

$DAB_{389}IL-4$ Sensitivity of Normal and Neoplastic Cells and Cell Lines

| Cell or Cell Line | Classification | $IC_{50}$ (M) |
|---|---|---|
| T cell origin | | |
| HUT 102/6TG | Human, CTCL, HTLV-I$^+$ | $2.9 \times 10^{-11}$ |
| C91/PL | Human, HTLV-I$^+$, transformed | $6.3 \times 10^{-11}$ |
| B cell origin | | |
| Raji | Human, Burkitt's lymphoma EBV$^+$ | $7.2 \times 10^{-10}$ |
| Myelomononuclear cell | | |
| U937 | Human, histiocytic lymphoma | $2.0 \times 10^{-9}$ |
| Normal PBMC | | |
| PHA activated T cells | Human | $1.6 \times 10^{-10}$ |
| Non-primate | | |
| Con A-activated normal splenic T cells | Rat | $>10^{-7}$ |

Preparation of $DAB_{389}IL-6$

A synthetic gene encoding human interleukin-6 was synthesized (Milligen/Biosearch 7500 DNA synthesizer). The IL-6 sequence (Revel et al., EPA 8611404.9) was modified to incorporate E. Coli preferred codon usage (deBoer et al., supra), and restriction endonuclease cleavage sites were added to facilitate subsequent cloning steps. The entire IL-6 coding sequence was inserted into pDW27 plasmid as described above for $DAB_{389}IL-4$.

Mixed Toxins

The cytotoxic portion of some molecules useful in the invention can be provided by a mixed toxin molecule. A mixed toxin molecule is a molecule derived from two different polypeptide toxins. Generally, as discussed above in connection with diphtheria toxin, polypeptide toxins have, in addition to the domain responsible for generalized eukaryotic cell binding, an enzymatically active domain and a translocation domain. The binding and translocation domains are required for cell recognition and toxin entry respectively. The enzymatically active domain is the domain responsible for cytotoxic activity once the molecule is inside a cell.

Naturally-occurring protein which are known to have a translocation domain include diptheria toxin, Pseudomonas exotoxin A, and possibly other peptide toxins. The translocation domains of diphtheria toxin and Pseudomonas exotoxin A are well characterized (see, e.g., Hoch et al., *Proc. Natl. Acad. Sci. USA* 82:1692, 1985; Colombatti et al., *J. Biol. Chem*. 261:3030, 1986; and Deleers et al., *FEBS Lett*. 160:82, 1983), and the existence and location of such a domain in other molecules may be determined by methods such as those employed by Hwang et al. *Cell* 48:129, 1987); and Gray et al. *Proc. Natl. Acad. Sci. USA* 81:2645, 1984).

One useful IL-2/mixed toxin hybrid molecule is formed by fusing the enzymatically active A subunit of *E. coli* Shiga-like toxin (Calderwood et al., *Proc. Natl. Acad. Sci. USA* 84:4364, 1987) to the translocation domain (amino acid residues 202 through 460) of diphtheria toxin, and to IL-2. This three-part hybrid molecule, SLT-A/DTB'/IL-2, is useful in the method of the invention in the same way as $DAB_{486}$IL-2 described above. The IL-2 portion of the three-part hybrid causes the molecule to attach specifically to IL-2R-bearing cells, and the diphtheria toxin translocation portion acts to insert the enzymatically active A subunit of the Shiga-like toxin into the targeted cell. The enzymatically active portion of Shiga-like toxin, like diphtheria toxin, acts on the protein synthesis machinery of the cell to prevent protein synthesis, thus killing the cell. The difference between these two types of hybrid toxins is the nature of their enzymatic activities: the enzymatic portion of $DAB_{486}$IL-2 catalyzes the ADP-ribosylation by nicotinamide adenin dinucleotide of Elongation Factor 2, thereby inactivating this factor which is necessary for protein synthesis, while the enzymatic portion of SLT-A/DTB'/IL-2 is a ribonuclease capable of cleaving ribosomal RNA at a critica site, thereby inactivating the ribosome. SLT-A/DTB'/IL-2 hybrid would therefore be useful as a treatment for the same indications as $DAB_{486}$IL-2, and could be substituted or used in conjunction with it if, for example, a patient's activated T-cells develop a resistance to $DAB_{486}$IL-2.

Linkage of Toxins to Binding Ligands

The binding ligand and the cytotoxin of useful hybrid molecules can be linked in several ways. If the hybrid molecule is produced by expression of a fused gene, a peptide bond serves as the link between the cytotoxin and the binding ligand. Alternatively, the toxin and the binding ligand can be produced separately and later coupled by means of a non-peptide covalent bond.

For example, the covalent linkage may take the form of a disulfide bond. In this case, if the binding ligand is a protein, e.g., IL-2, the DNA encoding IL-2 can be engineered to contain an extra cysteine codon as described in Murphy et al. U.S. Ser. No. 313,599, hereby incorporated by reference. The cysteine must be positioned so as to not interfere with the IL-2 binding activity of the molecule. For example, the cysteine codon can be inserted just upstream of the DNA encoding $Pro_2$ of the mature form of IL-2. The toxin molecule must be derivatized with a sulfhydryl group reactive with the cysteine the modified IL-2. In the case of a peptide toxin this can be accomplished by inserting a cysteine codon into the DNA sequence encoding the toxin. Alternatively, a sulfhydryl group, either by itself or as part of a cysteine residue, can be introduced using solid phas polypeptide techniques. For example, the introduction of sulfhydryl groups into peptides is described by Hiskey (*Peptides* 3:137, 1981). Derivatization can also be carried out according to the method described for the derivatization of a peptide hormone in Bacha et al. U.S. Pat. No. 4,468,382, hereby incorporated by reference. The introduction of sulfhydryl groups into proteins is described in Maasen et al. (*Eur. J. Biochem*. 134:32, 1983). Once the correct sulfhydryl groups are present, the cytotoxin and IL-2 binding ligand are purified, both sulfur groups are reduced; cytotoxin and ligand are mixed;, (in a ratio of about 1:5 to 1:20) and disulfide bond formation is allowed to proceed to completion (generally 20 to 30 minutes) at room temperature. The mixture is then dialyzed against phosphate buffered saline to remove unreacted ligand and toxin molecules. Sephadex chromatography or the like is then carried out to separate on the basis of size the desired toxin-ligand conjugates from toxin-toxin and ligand-ligand conjugates.

Assays for IL-2 Receptor Binding an IL-4 Receptor Binding

The IL-2R binding ability of various molecules can be measured using an IL-2R assay for high affinity (Ju et al., *J. Biol. Chem*. 262:5723, 1987) or intermediate affinity receptors (Rob et al., *Proc. Natl. ad. Sci. USA* 84:2002, 1987). The IL-4R binding activity of various molecules can be measured using the assay describe by Park et al. (*J. Exp. Med*. 166:176, 1984) or the assay described by Foxwell et al. (*Eur. J. Immunol*. 19:1637, 1989).

Assays for Toxicity

Molecules of the invention (both antibodies and hybrid molecules) can be screened for the ability to decrease viability of cells bearing the targeted receptor by means of assays such as those described below.

Toxicity towards IL-2R bearing cells can be tested as follows. Cultured HUT 102/6TG (Tsudo et al., *Proc. Natl. Acad. Sci. USA* 83:9694, 1986) or YT2C2 (Teshigiwari et al., *J. Exp. Med*. 165:223, 1987) cells are maintained in RPMI 1640 medium (Gibco, Grand Island, N.Y.) supplemented with 25 mM HEPES (pH 7.4), 2 mM 1-glutamine, 100 U/ml penicillin, 100 μg/ml streptomycin, and 10% fetal calf serum (Hazelton, Lenexa, Kans.). Cells are seeded in 96-well V-bottomed plates (Linbro-Flow Laboratories, McLean, Va.) at a concentration of $1\times10^5$ per well in complete medium. Putative toxins are added to varying concentrations ($10^{-12}$M to $10^{-6}$M) and the cultures are incubated for 18 hrs. at 37° C. in a 5% $CO_2$ atmosphere. Following incubation, the plates are centrifuged for 5 min. at 170×g, and the medium removed and replaced with 100 μl leucine-free medium (MEM, Gibco) containing 8 μCi/ml ($^3$H-leucine; New England Nuclear, Boston, Mass.). After an additional 90 min. at 37° C., the plates are centrifuged for 5 min. at 170×g, the medium is removed, and the cells are collected on glass fiber filters using a cell harvester (Skatron, Sterling, Va.). Filters are washed, dried, and counted according to standard methods. Cells cultured with medium alone serve as the control.

Toxicity towards cells bearing IL-4R may be tested by an assay similar to that describe above for IL-2R bearing cells, but utilizing MLA144 cells (Rabin et al. *J. Immunol.* 127:1852, 1981) or HUT 102/6TG cells, seeded at 1×10$^5$ cells per well and incubated for 40 hours.

Therapy

Generally, the molecules of the invention will be administered by intravenous infusion. They may also be administered subcutaneously. Dosages of molecules useful in the methods of the invention will vary, depending on factors such as whether the substance is a cytotoxin, a lytic antibody, or an cell receptor blocking molecule. In the case of toxic molecules the extent of cell uptake is an important factor; less permeable molecules must be administered at a higher dose.

More than 60 patients have received DAB$_{486}$IL-2 in Phase I/II clinical protocols. The molecule is well tolerated with the maximum tolerate dose (MTD) established by transient asymptomatic hepatic transaminase elevations in about 30% of patients treated at the MTD. Anti-tumor effects have been seen in approximately 40% of patients; responses were noted in B-cell leukemias and lymphomas, cutaneous T-cell lymphoma and Hodgkin's disease (LeMaistre et al., *Blood* 360a:abstract 1429, 1990; Woodworth et al., *Fourth International Conference on Human Retrovirology*, 1991). Serum concentrations of 10$^{-8}$M DAB$_{486}$IL-2 have been safely achieved in patients with IL-2 receptor expressing malignancies. Significant anti-tumor effects have been observed in highly refractory leukemia/lymphoma patients and these effects have occurred despite the presence of elevated soluble IL-2R levels in all patients. This observation is consistent with data which suggest that soluble IL-2R does not interfere with binding of IL-2 to the high affinity interleukin-2 receptor. Animal and human studies have demonstrated that DAB$_{486}$IL-2 has no general immunosuppressive effect (LeMaistre et al., supra; Woodworth et al., supra).

Experiments indicate that binding and internalization of DAB$_{486}$IL-2 by cell bearing the high affinity IL-2 receptor occurs within 30 minutes of exposure, resulting in maximal inhibition of protein synthesis within several hours. Therefore, the molecule should be effective even if the serum half-life is rather short.

For DAB$_{486}$IL-2 a typical course of therapy might be 0.025 to 0.3 mg/kg/day for 10 to 30 days. This course of treatment can be repeated several times to provide effective therapy.

Other Embodiments

The molecules described above act to decrease cell viability by directing a cytotoxin (or a lytic antibody) to a targeted cell. Also useful in method of the invention are molecules which interfere with the targeted cell's ability to utilize a cytokine.

Derivatives of IL-2 or other cytokines which block utilization of endogenous cytokine are useful for preventing proliferation of targeted cells. For example, activated cells deprived of IL-2 fail to proliferate and, in the absence of the essential anabolic stimulus provided by IL-2, will eventually die. With regard to HIV infection, if utilization of IL-2 is prevented, the infected process will be disrupted. The ability of a give IL-2 derivative to interfere with IL-2 function can be tested in an IL-2 bioactivity assay such as the one described by Ju et al. (*J. Biol. Chem.* 262:5723, 1987). Hybrid molecules in which the toxin has been rendered inactive can be also used to block a cytokine receptor. A non-toxic mutant diphtheria toxin molecule has been described (Uchida t al. *J. Biol. Chem.* 248:3838, 1973), and this molecule can be used to produce a non-toxic IL-2/diphtheria toxin hybrid. See Svrluga et al. U.S. Ser. No. 590,113, hereby incorporated by reference, for an example of such a hybrid molecule.

Monoclonal antibodies can be used to kill or neutralize cytokine receptor-bearing cells in a number of ways. As described above, anti-cytokine receptor antibodies fused to a toxin molecule can be used to deliver the toxin to receptor-bearing cells. Lytic anti-cytokine receptor antibodies can themselves kill cytokine receptor-bearing cells by activating complement. For example, monoclonal antibodies which activate complement can be used to destroy IL-2R-bearing cells. Complement inducing antibodies are generally those of the IgG1, IgG2, IgG3, and IgM isotypes. Monoclonal anti-IL-2R antibodies can be screened for those able to activate complement using a complement-dependent cytotoxicity test, as follows.

Human T-lymphocytes and EBV transformed B-lymphocytes are labeled with $^{51}$Cr sodium chromate and used as target cells; these cells are incubated with hybridoma culture supernatants and with complement, and then the supernatants are collected and counted with a gamma counter. Those supernatants exhibiting toxicity against activated T-lymphocytes, but not resting T- or B-lymphocytes, are selected (described in detail in by Leonard et al., *Proc. Natl. Acad. Sci. USA* 80:6957, 1983). The desired anti-IL-2 receptor antibody is purified from the supernatants using conventional methods. The specificity of the antibody can be demonstrated by showing that the activity is blocked by exogenous IL-2.

Also useful are antibodies which block binding and/or uptake of a cytokine. For example, monoclonal antibodies which interfere with the binding and/or uptake of IL-2 are useful in the method of the invention because IL-2R bearing cells deprived of IL-2 fail to proliferate. Blocking monoclonal antibodies (and other blocking molecules) can be tested for their ability to interfere with IL-2 bioactivity using the method of Ju et al.,(supra). Generally, assays useful for blocking molecules will be competitive binding assays which measure the ability of the molecule being to interfere with binding of one or more of the receptor's natural ligands.

Monoclonal antibodies useful in the method of the invention can be made by immunizing mice with human IL-2R$^+$ T-lymphocytes, fusing the murine splenocytes with appropriate myeloma cells, and screening the antibodies produced by the resultant hybridoma lines for the requisite IL-2R binding properties by means of an ELISA assay. Antibody production and screening can be performed according to Uchiyama et al. (*J. Immunol.* 126 1393, 1981). Alternatively, useful antibodies may be isolated from a combinatorial library produced by the method of Huse et al. (*Science* 246:1275, 1989).

The invention can employ not only intact monoclonal or polyclonal antibodies, but also an immunologically-active antibody fragment, for example, a Fab or (Fab)$_2$ fragment; an antibody heavy chain, an antibody light chain; a genetically engineered single-chain Fv molecule (Ladner et al., U.S. Pat. No. 4,946,778); or chimeric antibody, for example, an antibody which contains the binding specificity of a murine antibody, but in which the remaining portions are of human origin.

What is claimed is:

1. A method for inhibiting virus replication in a patient, said virus causing a disease state in said patient without transforming cells of said patient infected by said virus, said method comprising administering to said patient a hybrid molecule which specifically binds targets cells bearing a high affinity, interleukin-2 receptor induced by infection by said virus, said hybrid molecule comprising a first and a second portion, said first portion comprising a molecule that kills or interferes with proliferation of said cells bearing high affinity interleukin-2 receptor and said second portion comprising a molecule that specifically binds to the high affinity interleukin-2 receptor.

2. The method of claim 1 wherein said virus is human immunodeficiency virus.

3. The method of claim 1 wherein said virus is EBV.

4. The method of claim 1 wherein said interleukin-2 receptor is the high affinity interleukin-2 receptor.

5. The method of claim 1 wherein said molecule kills cells bearing said interleukin-2 receptor.

6. The method of claim 1 wherein said second portion comprises all or a binding portion of an antibody specific for said interleukin-2 receptor.

7. The method of claim 1 wherein said second portion comprises all or an interleukin-2 receptor binding portion of interleukin-2.

8. The method of claim 1 wherein said first portion comprises a cytotoxin.

9. The method of claim 8 wherein said cytotoxin is a fragment of a peptide toxin which is enzymatically active but which does not possess generalized eukaryotic receptor binding activity.

10. The method of claim 9 wherein said fragment of a peptide toxin comprises fragment A of diphtheria toxin and enough of fragment B of diphtheria toxin to form a pore in a cell membrane.

11. The method of claim 10 wherein said molecule is $DAB_{486}IL\text{-}2$.

12. The method of claim 10 wherein said molecule is $DAB_{389}IL\text{-}2$.

13. The method of claim 10 wherein said molecule is $DAB_{486}IL\text{-}4$.

14. The method of claim 10 wherein said molecule is $DAB_{486}IL\text{-}6$.

15. The method of claim 1 wherein said molecule comprises all or a binding portion of an antibody specific for said interleukin-2 receptor.

16. The method of claim 15 wherein said antibody is a complement activating antibody.

17. A method for inhibiting HIV replication in a patient, comprising administering to said patient a hybrid molecule which specifically targets cells bearing an interleukin-4 receptor induced by infection by HIV, said hybrid molecule comprising a first and a second portion, said first portion comprising a molecule that kills or interferes with proliferation of said cells bearing an interleukin-4 receptor and said second portion comprising a molecule that specifically binds to the interleukin-4 receptor.

18. The method of claim 17 wherein said molecule is $DAB_{389}IL\text{-}4$.

19. A method for inhibiting HIV replication in a patient, comprising administering to said patient a hybrid molecule which specifically targets cells bearing an interleukin-6 receptor induced by infection by HIV, said hybrid molecule comprising a first and a second portion, said first portion comprising a molecule that kills or interferes with proliferation of said cells bearing an interleukin-6 receptor and said second portion comprising a molecule that specifically binds to the interleukin-6 receptor.

20. The method of claim 19 wherein said molecule is $DAB_{389}IL\text{-}6$.

* * * * *

UNITED STATES PATENT AND TRADEMARK OFFICE
CERTIFICATE OF CORRECTION

PATENT NO. : 6,074,636
DATED : June 13, 2000
INVENTOR(S) : Nichols

It is certified that error appears in the above-identified patent and that said Letters Patent is hereby corrected as shown below:

Column 2,
Line 22, after "meant" insert --a--.

Column 3,
Line 29, "contribute" should read --contributes--.

Column 6,
Line 28, before "powerful" insert --a--.

Column 9,
Line 27, "des bed" should read --described--.
Line 59, "consist" should read --consists--.

Delete Column 11, line 65 - Column 12, line 3 up to "p. 24."

Column 12,
Line 6, delete "lane 4" and insert --data not shown--.
Line 6, delete "(lanes 3 and 7)" and insert --data not shown--.
Line 7, delete "lane 5" and insert --data not shown--.
Line 8, delete "lane 9" and insert --data not shown--.
Lines 8-9, delete "lane 8" and insert --data not shown--.
Line 10, delete "(lanes 2 and 6)" and insert --data not shown--.
Line 65, "incubate" and insert --incubated--.

Column 13,
Line 56, "ny" should read --any--.
Line 63, "3" should read --2--.

Column 14,
Line 33, "result" should read --results--.

Column 16,
Line 13, "phas" should read --phase--.

UNITED STATES PATENT AND TRADEMARK OFFICE
CERTIFICATE OF CORRECTION

PATENT NO. : 6,074,636
DATED : June 13, 2000
INVENTOR(S) : Nichols

It is certified that error appears in the above-identified patent and that said Letters Patent is hereby corrected as shown below:

Column 17,
Line 39, "cell" should read --cells--.
Line 62, "give" should read --given--.

Column 19,
Line 2, "targets" should read --target--.
Line 6, after "bearing" insert --a--.

Signed and Sealed this

Fourteenth Day of August, 2001

*Attest:*

*Attesting Officer*

NICHOLAS P. GODICI
*Acting Director of the United States Patent and Trademark Office*